(12) United States Patent
Koch (10) Patent No.: US 8,121,465 B2
(45) Date of Patent: Feb. 21, 2012

(54) MOBILE FLUE GAS GENERATOR AND METHOD FOR TESTING A FLUE GAS INDICATOR

(75) Inventor: Hubert Koch, Mönchengladbach (DE)

(73) Assignee: No Climb Products Limited, Welham Green, Hertfordshire (GB)

( * ) Notice: Subject to any disclaimer, the term of this patent is extended or adjusted under 35 U.S.C. 154(b) by 666 days.

(21) Appl. No.: 10/477,301

(22) PCT Filed: May 7, 2002

(86) PCT No.: PCT/DE02/01650
§ 371 (c)(1),
(2), (4) Date: May 20, 2004

(87) PCT Pub. No.: WO02/091326
PCT Pub. Date: Nov. 14, 2002

(65) Prior Publication Data
US 2004/0197092 A1 Oct. 7, 2004

Related U.S. Application Data

(60) Provisional application No. 60/290,133, filed on May 10, 2001, provisional application No. 60/291,880, filed on May 18, 2001.

(30) Foreign Application Priority Data

| | | |
|---|---|---|
| May 9, 2001 | (DE) | 101 22 572 |
| Aug. 15, 2001 | (DE) | 101 39 033 |
| Oct. 1, 2001 | (WO) | PCT/DE01/03747 |
| Jan. 9, 2002 | (DE) | 102 00 584 |

(51) Int. Cl.
F22B 1/28 (2006.01)
F02M 15/04 (2006.01)

(52) U.S. Cl. .................... 392/399; 261/142

(58) Field of Classification Search ............ 392/386, 392/387, 390, 393, 402, 403, 404, 405, 406; 261/142, DIG. 65; 446/24, 484
See application file for complete search history.

(56) References Cited

U.S. PATENT DOCUMENTS

| | | | | |
|---|---|---|---|---|
| 2,662,332 A | * | 12/1953 | McIntire | 43/129 |
| 2,850,615 A | * | 9/1958 | Luse, Jr. et al. | 434/49 |
| 3,002,237 A | * | 10/1961 | Spexarth | 43/129 |
| 3,729,979 A | | 5/1973 | Wiberg et al. | |
| 4,326,119 A | * | 4/1982 | Swiatosz | 392/397 |
| 4,439,341 A | * | 3/1984 | Swiatosz | 516/5 |
| 4,570,851 A | * | 2/1986 | Cirillo | 236/93 R |
| 4,864,146 A | | 9/1989 | Hodges et al. | |
| 5,170,148 A | | 12/1992 | Duggan et al. | |
| 5,611,620 A | | 3/1997 | Wantz | |

(Continued)

FOREIGN PATENT DOCUMENTS

| | | |
|---|---|---|
| DE | 199 26 773 | 12/2000 |
| FR | 2 583 553 | 12/1986 |
| JP | 07200980 | 8/1995 |
| WO | 94/25496 | 11/1994 |

*Primary Examiner* — Sang Paik
(74) *Attorney, Agent, or Firm* — Collard & Roe, P.C.

(57) ABSTRACT

The aim of the invention is to improve a mobile flue gas generator and to simplify a method for testing a flue gas indicator. The invention is characterised in that a mobile flue gas generator for simulating a real flue gas is proposed, whereby the mobile flue gas generator comprises an electric heating device for generating the flue gas.

12 Claims, 4 Drawing Sheets

U.S. PATENT DOCUMENTS

| | | | |
|---|---|---|---|
| 5,644,071 A | 7/1997 | Wagner | |
| 5,810,253 A * | 9/1998 | Ohayon | 239/43 |
| 6,393,212 B1 * | 5/2002 | Hutchinson | 392/491 |
| 6,543,247 B2 * | 4/2003 | Strauss | 62/259.3 |

* cited by examiner

MOBILE FLUE GAS GENERATOR AND METHOD FOR TESTING A FLUE GAS INDICATOR

CROSS REFERENCE TO RELATED APPLICATIONS

Applicant claims priority under 35 U.S.C. §119 of German application number 101 22 572.5, filed on May 9, 2001; U.S. application No. 60/290,133 filed on May 10, 2001; U.S. application No. 60/291,880 filed on May 18, 2001; German application number 101 39 033.5 filed on 15 Aug. 2001; German application number PCT/DE01/03747 filed on Oct. 1, 2001; and German application number 102 00 584.2 filed on Jan. 9, 2002. Applicant also claims priority under 35 U.S.C. §365 of PCT/DE02/01650 filed on May 7, 2002. The international application under PCT article 21(2) was not published in English.

The invention relates to a mobile flue gas generator for simulating a real flue gas and a method for testing a flue gas indicator, in which a flue gas generator that has been brought into the vicinity of the flue gas indicator generates a flue gas, using a test medium, and the flue gas initiates testing of the flue gas indicator.

In order to test flue gas indicators with regard to their ability to function, mobile flue gas generators are known, among other things. These flue gas generators are held against a flue gas indicator until the latter triggers an alarm as a result of the flue gas of the flue gas generator.

This involves devices that carry a test aerosol in a pressure flask. A disadvantage of these devices is that they are disadvantageous to handle, because of the pressure flask, among other things. Also, triggering of such a device is generally disadvantageous to perform, by means of a triggering mechanism that is generally complicated and difficult to use.

Another type of testing devices is known from the company Hekatron GmbH. This testing device uses a fumigator rod that is inserted into a housing of the device, in order to generate flue gas, whereby the housing must be closed again with great care, since it must be assured that a gasket ring that seals a bottom and a top of the housing is not damaged. During the actual testing of the flue gas indicator, the hose top of the testing device is then held against the flue gas indicator, whereby the flue gas must be pressed out of the hose tip against the flue gas indicator, by means of compressing a rubber ball.

In addition to the complicated handling as described above, a ventilation hole of the housing must be manually closed off with a finger during a pumping cycle, so that no flue gas can escape from this ventilation hole while the rubber ball is being compressed. In order to fill the compressed rubber ball with air again, the ventilation hole of the housing is now released, so that fresh air can flow back into the rubber ball of the testing device, by way of this hole. Such a method is extremely complicated, particularly if the flue gas indicators to be tested are suspended high up on a ceiling.

As described, known testing devices for flue gas indicators have a rather complicated method of operation. In addition, the test procedure using the known testing devices quite often has to be performed several times, due to frequent failed attempts. It is also disadvantageous, in this connection, that long waiting times result from an extended stay of the test aerosols or the smoke of the fumigator rod in or at the flue gas indicator, until the flue gas indicator is reset from the alarm state into the normal state.

The invention has the aim of developing flue gas generators further, and thereby simplifying testing of a flue gas indicator.

The task on which the invention is based is solved by a mobile flue gas generator for simulating a real flue gas, whereby the mobile flue gas generator has an electric heating device for generating the flue gas. Such an electric heating device can be present in many different forms, particularly preferably, however, as a heat generator that has an electrically conductive wire. It is advantageous, in the case of this heat generator, that heat can be generated without using an open flame. In order to generate heat, a current is merely passed through the wire, so that the latter heats up. Thus, the electric heating device can be used as a heat generator, to particular advantage.

In the present case, the term "flue gas" is understood to mean any gaseous media that particularly contain solid particles. However, gases that explicitly do not contain any solid particles are also covered by the term "flue gas" in the sense of the invention.

Accordingly, the term "flue gas indicator" includes all technical devices that can detect a flue gas with solid particles as well as a flue gas without solid particles. It is understood that the generation of a flue gas with solid particles can also be replaced by the generation of a gas without solid particles. This is particularly advantageous if the function of a gas indicator that responds to the presence of a gas is supposed to be tested.

Because of the characteristic that the electric heating device can be used as a heat generator, it is possible to use the flue gas generator according to the invention not only for testing a flue gas indicator or gas indicator. Instead, the flue gas generator according to the invention can be used, over and above this, for testing a heat indicator. In particular, a heat generator is created in this way, which has a solid body that gives off heat radiation when activated. For example, this is an infrared lamp that gives off heat radiation and thereby activates a heat indicator.

A preferred embodiment variant provides that the heating device is an electric resistor. Preferably, this is a commercially available ohmic resistor, which can be inserted into an electrically conductive wire in simple manner. In particular, the ohmic resistor reinforces the heat generation, for one thing, and increases the surface that heats up, which is able to give off heat, for another thing.

It is particularly advantageous if the mobile flue gas generator has an electric blower. In this connection, the electric blower can be a small fan, which draws in a volume of air from the surroundings, and then passes it through the mobile flue gas generator, whereby the volume of air guides the flue gas through at least one opening of the mobile flue gas generator, in the direction of a flue gas indicator. It is possible to use any other device that is able to accelerate a volume of air, instead of the fan. It is particularly advantageous if a volume of air is accelerated in pulse-like manner using the blower. In this way, the flue gas can be brought to a flue gas indicator in pulse-like manner and therefore in a high concentration.

Another embodiment variant provides that the mobile flue gas generator has an electric energy source. By means of this electric energy source, a power supply to the heating device and the fan is guaranteed, for example. In this connection, a public power net or a solar power unit can serve as the electric energy source. Preferably, however, the electric energy source possesses a battery or a rechargeable battery. By means of the battery or rechargeable battery, in particular, the mobile flue gas generator is configured as a power-independent component and is independent of a power test set.

It is particularly advantageous if the mobile flue gas generator can be electrically triggered. In this connection, a flue gas is generated only if the heating device, i.e. the heat generator is electrically triggered, whereby then a current of the electric energy source flows through the heating device, i.e. through the heat generator.

Furthermore, it is proposed that the mobile flue gas generator has a heat conduction body. For example, the heat conduction body is produced from an electrically conductive sheet metal, so that the heatable surface increases due to the relatively large surface of the sheet metal as compared with the surface of the wire. It is particularly advantageous if the heat conducting body is implemented in the form of an electric resistor. For example, this resistor is a commercially available resistor, so that in this way, a product of mass production can be used to increase the performance of the heating device.

It is advantageous if the heat conducting body has a porous body. The porosity of the body allows absorption of a substance according to the nature of a sponge, so that the absorbed substance is in intimate contact with the porous body, with the heat conducting body, preferably in the region of the pores. If, in this connection, the heat conducting body, i.e. the electric resistor is heated, the substance deposited on the porous body or embedded in the porous body evaporates, thereby generating the flue gas.

If the heat conducting body itself does not have a porous body, it is advantageous if a porous component is arranged on the heat conducting body. A substance can be embedded and, as necessary, made to smoke, on this porous component, as well.

In order to achieved a flue gas generation at a targeted location of the porous body or the porous component, for example, and/or in order to prevent uncontrolled exit of the substance from the porous body or from the porous component, it is advantageous if the porous body or the porous component has a mantling that is preferably structured as a heat-resistant film. By means of the heat-resistant film, the substance heated by the porous body or by the porous component is prevented from evaporating at an undesirable location of the porous body or the porous component.

Accordingly, it is advantageous if the mantling has at least one opening through which the heated substance evaporates or smokes.

According to another embodiment, it can be provided that the mobile flue gas generator has a heat chamber that is filled at least in part with the test medium. It is advantageous if the flue gas is generated using the test medium.

Since it can be difficult, with regard to installation or maintenance work, to transport cartridges that are under pressure, or fluid-filled containers, it is proposed that the test medium has a solid body that evaporates or smokes when heated, at least in part. This solid body can be a plastic element or a wax. The wax is preferably heated by means of a resistor element that heats up when current flows through it, so that in this way, at least a part of the wax or of the solid body evaporates or smokes because of the heating.

The test medium can be solid or liquid; it is particularly advantageous if the test medium comprises a gel-like material that evaporates or smokes, at least in part, when heated. For example, the electric heating device or the heat conducting body, particularly the commercially available resistor, is located in the gel-like test medium, so that part of the test medium is heated to such a degree, due to the immediate proximity of the heating device, that it evaporates or smokes into a gaseous state, and that the mobile flue gas generator generates a flue gas in this connection.

The gel-like material can be a water-clear gel without an odor. Gels made from hydrocarbons in the sector of the white oils, which are produced by adding a gel-forming agent, are well suitable. Such gels preferably have a boiling point that lies above 250° C. In the present case, the melting point preferably lies at about 70° C. to 90° C. This has the result that in the case of such substances, practically no evaporation of ingredients takes place at room temperature. Therefore any burden for the ambient air can be reliably precluded also for the storage of the substances or from the supply contained in the testing device.

In practice, long-chain aliphatic hydrocarbons are preferably used. Particularly if an amount of about a milligram is evaporated per test procedure, this evaporated amount is without any health relevance, since aliphatic long-chain hydrocarbons result in mechanical irritation of the upper respiratory tract only at high concentrations. The substances described furthermore have the advantage that they settle in the vicinity of substance release and that the released amounts do not result in either corrosion or other negative influences on adjacent electronic or mechanical components.

For this reason, such a substance can advantageously be used, particularly in all of the flue gas generators described in this application.

It was found that it is advantageous if the test medium only has a mass of less than 5 g, preferably less than 1 g. It is advantageous that the mobile flue gas generator according to the invention only requires approximately 0.001 g of the gel-like test medium, so that up to 600 tests are conducted with the mobile flue gas generator according to the invention, without having to refill the mobile flue gas generator with a test medium. This corresponds to a usage period of approximately 40 years, with a monthly test cycle. Because of the small amount of test medium, the weight of the mobile flue gas generator is significantly reduced.

According to another embodiment of the invention, it is provided that the heating device is in active contact with the test medium. In this way, the structure of a mobile flue gas generator is very simply designed, whereby additional means for flue gas development are superfluous.

Preferably, the heating device is arranged in the heat chamber, so that it is advantageously in the immediate vicinity of the test medium.

In order to transport the generated flue gas out of the heat chamber in particularly effective and dynamic manner, it is advantageous if a blower is arranged in the heat chamber. Preferably, the blower is arranged at an air inlet opening of the heat chamber or in the vicinity of an air inlet opening of the heat chamber, so that when the blower is activated, a stream of air is generated that is passed through the heat chamber filled with flue gas. In this connection, the flue gas, together with the air stream, gets out of the heat chamber into the immediate vicinity of the flue gas indicator, by means of an exit opening.

It is proposed that the heating device has a temperature of more than 80° C., preferably a temperature of more than 110° C., when the test medium is made into smoke.

Likewise, it is proposed that the heating device has a temperature of less than 200° C., preferably a temperature of less than 160° C., when the test medium is made into smoke.

It is particularly advantageous if the test medium evaporates or smokes at approximately 150° C.

It is advantageous if the mobile flue gas generator has a collection device in which a flue gas that has been generated is accumulated, at least temporarily. In particular, the heat chamber of the mobile flue gas generator can represent such a collection device. In this way, the mobile flue gas generator has a particularly simple structure. It is advantageous if the heat chamber is designed in such a manner that first a flue gas is generated in a closed or almost closed heat chamber, and only gets out of the heat chamber after a certain period of time of flue gas generation.

In order to guide a stream of air through the collection device, and thereby to entrain the flue gas that has been generated, it is advantageous if the collection device has at least one inlet opening and/or at least one exit opening. Preferably, in this connection, the openings are sized or structured in such a manner that a flue gas that has been generated does not escape from the collection device or from the heat chamber, or escapes only in an amount that can be ignored, unless it is actively transported. The active transport can be implemented by means of the air stream generated by the blower.

An embodiment variant provides that the collection device has at least one means for closing it. This means for closing is, for example, a simple flap or a valve, or the like. Preferably, such a means is arranged in one opening or in all of the openings described above. In this connection, it is not absolutely necessary that the means for closing seals off the collection device at 100%.

Instead, it is sufficient to close off the collection device in such a manner that flue gas that has been generated cannot exit from it, or can exit only in a small amount, without an artificially generated air stream or the like, for example.

It is advantageous if the means for closing has a wire having a structure that is temperature-dependent. By means of such a wire, it is possible to activate a flap, for example, in such a manner that it closes the collection device or, in contrast, at least partly opens it. In this connection, the wire preferably has such a structure that it is shortened or lengthened by an electrical current and the accompanying temperature increase.

It is particularly advantageous if the means for closing has a nitinol wire. Nitinol wire contracts, for example, if a current of 3.5 volts flows through it, as a result of the heating that occurs, and then expands again after cooling. In this connection, the contraction of the nitinol wire can be advantageously used to open the flap.

It is understood that as an alternative to this, any other actor or also a linear motor, for example, can be used for this purpose.

It is furthermore proposed that the collection device has a flue gas inflow opening. By means of this flue gas inflow opening, it is possible that a flue gas that is not generated directly in the collection device gets into the collection device by way of this flue gas inflow opening. For example, the flue gas is generated in the heat chamber of the mobile flue gas generator, and gets into the collection device by way of the flue gas inflow opening.

It is particularly advantageous if the collection device has a flue gas sensor and/or a gas sensor. In order to test the flue gas generator with regard to the generation of flue gas, or in order to determine whether a sufficient amount of flue gas was generated and is present in the collection device, it is advantageous if the corresponding flue gas sensor is arranged directly in the collection device of the flue gas generator. For example, by activating the flue gas sensor, a user of the flue gas generator is given an optical or acoustical message concerning the point in time at which sufficient flue gas for testing a flue gas indicator is available, so that the user activates a trigger that opens the outlet of the collection device or the heat chamber, after having brought the flue gas generator into the vicinity of a flue gas indicator.

It is particularly advantageous if the collection device has a changeable cross-section. By means of the changeable cross-section, different pressures and flows are brought about within the collection device, and this has a positive effect on the spread of the flue gas.

A structurally simple variant provides that the collection device has a diffusor. By means of the diffusor, different flow velocities as well as different pressures can be brought about in the collection device.

A preferred embodiment provides that the collection device has a Venturi tube. By means of the Venturi tube, different pressures and flow velocities can also be achieved and used in targeted manner.

A preferred embodiment provides that the mobile flue gas generator has a housing that is at least partly elastic. Particularly in the region of the heat chamber or the collection device, it is advantageous if the housing consists of a ductile material that can easily be compressed by means of a pump movement, for example, and thereby reduces the volume of the heat chamber or of the collection device. By means of such a volume reduction, a flue gas that has been generated is regularly expelled out of the heat chamber or out of the collection device, so that as great and dense a flue gas volume as possible gets to the flue gas indicator within the shortest possible period of time.

An advantageous further development of the invention consists of arranging a supply device and/or a metering device as well as a blower on the elastic housing. Such devices are arranged on the housing by way of a positive-lock connection or a friction-lock connection, for example.

It is advantageous if these devices, in particular, are plugged into the housing of the mobile flue gas generator. For example, the housing is designed in such a manner that the plugged-in devices are additionally fixed in place on the housing by means of a rubber lip. This rubber lip surrounds the plugged-in device at least in part, so that the device can be removed from the housing only if the rubber lip is "pressed sideways."

Furthermore, the elastic housing also takes on a protective function with regard to damage to the devices. For example, the devices arranged in the elastic housing are very well protected against impacts because of this, since the elastic housing can absorb at least part of the impact energy.

It is understood that the devices mentioned above can be not only plugged in but also arranged on or in the housing by means of a threaded connection.

The housing is preferably produced from a plastic or an elastomer, in this connection, so that it demonstrates only a relatively soft resistance with regard to other objects. This also reduces the risk of damage to other objects.

A particularly preferred embodiment variant provides that the mobile flue gas generator has at least one holding means for arranging at least one component on the mobile flue gas generator. In this way, the devices described above can be arranged in or on the housing of the mobile flue gas generator in particularly simple manner.

It is advantageous if a supply device that contains a supply of a test medium is arranged in a holding means. Using the holding means, the supply device can be affixed on or in the mobile flue gas generator in particularly simple manner. In this way, an exchange of supply devices with different test media, if necessary, is made very simple.

In order to guide a test medium that is present in the supply device into the vicinity of the heating device in simple manner, it is advantageous if the holding means in which the supply device is arranged communicates with an output device for issuing a test medium.

In this connection, the output device is preferably arranged in the immediate vicinity of the heating device, so that the test medium that exits by way of the output device quickly enters into contact with the heating device and evaporates or smokes when doing so. Furthermore, it is advantageous if the output device is arranged at such a distance from the heating device that the heating device does not damage the output device as the result of a disadvantageous temperature influence.

In order to structurally guarantee, in simple manner, that the test medium gets from the supply device to the output device, it is advantageous if the housing has at least one bore that is used as a test medium feed, whereby the test medium feed connects a holding means of the supply device and an output device for a test medium with one another.

It is advantageous if the supply device is a disposable component. In this way, simple handling with regard to a refilling process of the test medium is guaranteed, since an empty supply device can be replaced with another supply device. In addition to this simple and preferred embodiment variant, it is also possible to refill the supply device after the test medium has been used up.

A supply device is structured in simple manner if the supply device has a cylinder and a piston. In particular, a disposable supply device is produced in simple manner in this way, if the piston or the piston rod is shorter than the actual cylinder. Therefore, the piston rod, in particular, can no longer be moved out of the cylinder once the piston has been completely pressed in, thereby making refilling of the cylinder almost impossible, or only possible at great effort. This particularly prevents improper refilling of the supply device. This reduces the risk that a substance not intended for the mobile gas generator contaminates the heating device or that a flue gas that might be harmful to health is generated by the device.

Furthermore, it is advantageous if a metering device is arranged in a holding means. By means of the metering device, it is possible to precisely meter a test medium amount to be issued from the supply device. Therefore the consumption of the test medium can be precisely adjusted.

The supply device can communicate with the metering device in particularly simple manner if the metering device has a holding region for holding the supply device. In this connection, the supply device can be attached to the holding region of the metering device either with a non-positive or a positive lock.

Furthermore, it is advantageous if the metering device has a setting means that preferably catches. Using the setting means of the metering device, it is possible to issue a predetermined amount of a test medium from the supply container, by means of the output device, to the heating device, in particularly simple manner, so that as accurate as possible a predetermined amount of test medium is evaporated or made into smoke on the heating device.

In this connection, the metering device is preferably set manually, so that the piston is moved in the cylinder by the path x, for example. It is understood that in addition to manual activation of the metering device, electrical or electronic activation can also be provided.

Furthermore, the mobile flue gas generator can have a coordination means that coordinates the activation of the blower and the activation of the metering device. For example, the operation of the fan and of the metering device is electrically regulated or controlled. Preferably, the operating state of the heating device is also controlled using the coordination means.

In this connection, it is possible to preheat the heating device first, after a start procedure of the testing, and subsequently, after about two seconds, the fan of the blower starts to run and generates a stream of air that transports the flue gas that has been generated out of the heat chamber.

In order to have enough test medium available at the heating device, for example, it is advantageous if the metering device automatically transports test medium from the supply device in the direction of the heating device. This can be done in cycles, which are dependent on the output of the heating device, for example.

Furthermore, it is possible to operate the blower in pulsed manner, so that intervals are produced in which the blower generates a greater stream of air or in which the ventilator generates a comparatively lesser stream of air.

Likewise, it is advantageous if the heating device is supplied with energy in pulsed manner. For example, the temperature of the heating device can be brought to an evaporation temperature $tV=150°$ C. and held there, in this way. Otherwise there is the risk that overly great heating of the heating device can cause damage to the mobile flue gas generator.

In the sense of the invention, the term "pulsed" is understood to mean that making energy available for the devices in question is varied, preferably automatically.

Furthermore, it is proposed that the mobile flue gas generator has a capillary device. For example, one end of a capillary tube is arranged in a housing in which the test medium is located. The other end of the capillary tube, on the other hand, has a heating device or is directly and actively connected with the heating device. Part of the test medium always moves through the capillary tube by means of adhesion forces, into the region of the heating device, which assures that the test medium is made into smoke when it is activated.

Another embodiment variant provides that the flue gas generator has a fluid container and an ignition device. The fluid container can also be configured as a pressurized container, so that it allows the fluid to be sprayed. The fluid, in interaction with the heating device, can generate a gas by means of evaporation or combustion of the fluid, whereby this gas then is ignited by an ignition device, so that a flue gas and/or heat is/are generated in this way.

Preferably, the heating device can be remote-controlled, so that it is only turned on when needed. This is the case, for example, if the mobile flue gas generator according to the invention is held in the immediate vicinity of a flue gas indicator. Such a remote control can be structured by means of a line or in wireless manner, and makes it possible to trigger the mobile flue gas generator at any desired time.

In order to avoid overheating of the test medium, it is advantageous if the mobile flue gas generator has a time clock. This creates the possibility of limiting the heating period of the heating device in terms of time, so that a switch must be activated, for example, in order to activate the heating device again.

A particularly preferred embodiment variant provides that the flue gas generator has an interface to a network. For example, the flue gas generator is connected with the local network of a building, so that the flue gas generator can be controlled from a central device. In this connection, the interface can be structured to be wired or wireless. It is also possible that the flue gas generator has a contact not only to a local network, but rather also to a wide-area network. For example, a flue gas generator is connected with a central security service by means of a wide-area network, and this service is not located directly in the building of the flue gas indicator to be tested.

The aim of the invention is also accomplished by a method for testing a flue gas indicator, in which a flue gas generator brought into the immediate vicinity of the flue gas indicator generates a flue gas by means of a test medium, and the flue gas initiates testing of a flue gas indicator, whereby the test medium is made into smoke by an electric heating device.

Furthermore, it is advantageous if the flue gas is transported to the flue gas indicator by means of an electric blower, in this connection.

It is advantageous in this method that according to the invention, the flue gas is generated by an electric heating device, in which a test medium is made into smoke by the electric heating device. In this connection, it is particularly advantageous that only a very small amount of a test medium is used up for generating the flue gas.

It is also advantageous that the flue gas is blown directly into or onto the flue gas indicator by means of an electric blower of the mobile flue gas generator, so that targeted application of smoke to the flue gas indicator occurs, whereby the effectiveness of a flue gas indicator test is significantly increased by means of the targeted effect of the method.

Once the test sequence of the flue gas indicator has been successfully initiated, it is particularly advantageous if the flue gas indicator is ventilated immediately after smoke has been applied, so that the test is terminated as quickly as possible. By means of this targeted subsequent ventilation by means of the mobile flue gas generator, the risk of an undesirable deposit of flue gas particles in the flue gas indicator, but also within the mobile flue gas generator, is reduced.

Furthermore, it is advantageous that the entire test procedure is significantly accelerated by means of the active ventilation of the flue gas indicator, thereby making it possible to test more flue gas indicators per time unit, among other things.

A further embodiment provides that the flue gas that has been generated is collected before it gets out of the mobile flue gas generator. It is advantageous if first a certain volume of flue gas is collected, which is sufficient to activate a flue gas indicator or a gas indicator. Another method variant provides that a changeable volume stream is generated to transport the flue gas.

It is advantageous if the rotor of the blower changes its speed of rotation for this purpose.

This can be implemented in particularly simple . manner, particularly if energy is made available to the blower discontinuously during testing.

In order to set the heating device to a desired temperature and to keep it there, it is advantageous if energy is made available to the heating device discontinuously, particularly during testing.

In order to be able to evaporate or smoke a test medium in optimal manner, it is advantageous if the heating device is preheated before a test medium is passed to it.

Another method variant provides that the function of a heat indicator is tested by means of the heat generated by the heating device. Preferably, this is carried out without generating any flue gas. In this connection, the mobile flue gas generator can also be advantageously used for simulating heat, so that not only a flue gas indicator or a gas indicator, but furthermore also a heat indicator can be tested with the flue gas generator according to the invention. Therefore almost all fire indicators can be tested by means of a single mobile testing device, so that investment costs with regard to different testing devices can be saved in this way. It is particularly advantageous if the heat that is generated is blown towards a heat indicator by means of the activated blower, for support.

It is understood, in this connection, that the combination of the heat generator and the blower, particularly their common use for testing a heat generator, are essential to the invention even independent of the other characteristics of the invention.

It is advantageous if the mobile flue gas generator is activated by means of a central monitoring facility, whereby the flue gas that was generated is detected by a flue gas indicator, and the flue gas indicator is activated by this, whereby the flue gas indicator transmits a data signal.

A monitoring facility is understood to mean a central facility, for example, in which the security-relevant functions of a building are monitored.

A preferred method variant provides that the data signal is transmitted to a central monitoring facility and/or to an emergency facility. For example, the central monitoring facility is present directly in a building, so that all of the steps necessary for testing can be coordinated from there.

It is also advantageous if the data signal is additionally or exclusively transmitted to an emergency facility. An emergency facility is, for example, a local fire department or another rescue service.

If the data signal is transmitted in parallel to the central monitoring facility and also to the emergency facility, it is advantageous if information about an upcoming test is provided to the monitoring facility and/or the emergency facility before a test is conducted. For example, the information contains data concerning the date and time of testing, as well as about the type of test and the duration of the test. Preferably, the emergency facility is automatically informed by the central monitoring facility.

According to the invention, it is proposed that at least one data line between the central monitoring facility and the emergency facility and/or at least one data line between at least one gas indicator and the emergency facility is deactivated. In order not to put the emergency facility, for example the fire department, into emergency status by mistake, it is advantageous if the data line to this emergency facility is deactivated, at least temporarily.

Finally, it is proposed that a test protocol is sent to the monitoring facility and/or the emergency facility. Once the test has been concluded, it is advantageous if the emergency facility is informed about the current status of the gas indicators of a building, for example.

Other advantages, aims, and properties of the present invention are described on the basis of an explanation of the attached drawings, in which a mobile flue gas generator is shown as an example.

Figure 1:
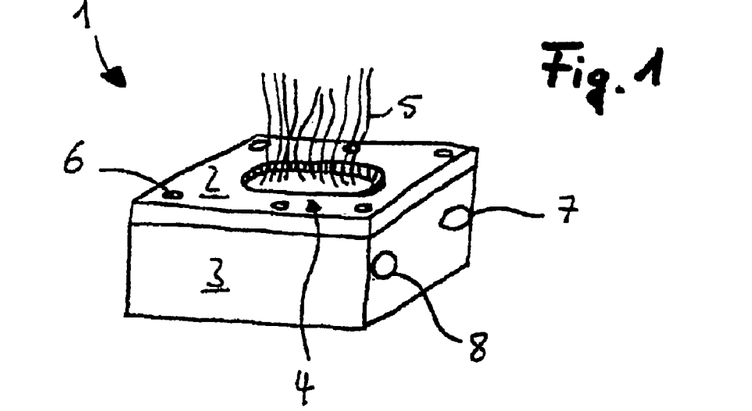
FIG. 1 a heat chamber divided into two parts.

The heat chamber 1 divided into two parts in FIG. 1 has a closing cover 2 and a base housing 3. The closing cover 2 has an opening 4 in its center, through which a flue gas 5 that has been generated rises. The closing cover 2 is screwed onto the base housing 3 by means of a plurality of screws 6 (numbered here only as an example).

The base housing has two bores 7 and 8 on one side, which hold plug-in contacts for an electrical connector (not shown here).

Figure 2:
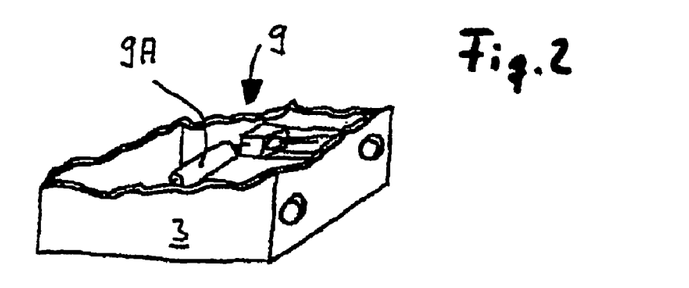
FIG. 2 a heat chamber in partial cross-section.

FIG. 2 shows the base housing 3 of the two-part heat chamber 1 in a broken view. A heating device 9 is arranged in the interior of the base housing 3. The heating device 9 has a resistor 9A.

Figure 3:
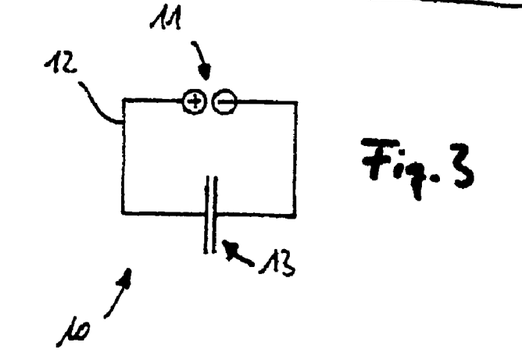
FIG. 3 a rechargeable battery power source, schematically.

FIG. 3 fundamentally shows the simple structure of an electric current circuit 10 of a mobile gas generator 29 according to the invention. Here, a rechargeable battery 11, which is connected with a heat conducting body 13 (capacitor, ohmic resistor) by means of a wire connection 12, serves as a power source.

Figure 4:
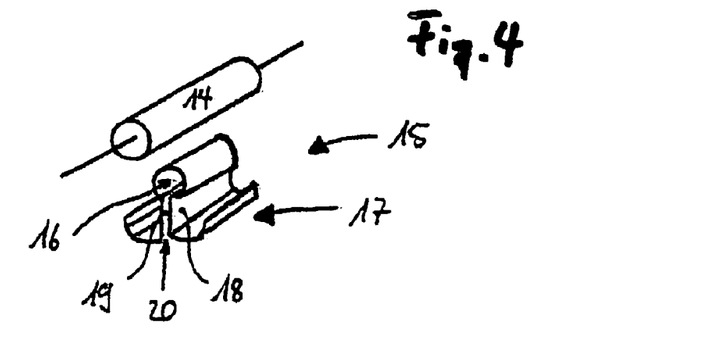
FIG. 4 a resistor and a cuff having capillary surfaces.

FIG. 4 shows an ohmic resistor 14 as well as a capillary cuff 15, whereby the diameter of the resistor 14 corresponds to the diameter of the capillary cuff 15 in a region 16.

The capillary cuff 15 is arranged in a gel-like test medium (not shown here) with its lower region 17, whereby the gel-like test medium moves in the direction of the arrow 20, between the two capillary interior surfaces 18 and 19, towards the resistor 14, in the interior of the capillary surfaces 18 and 19, by means of capillary forces.

Figure 5:
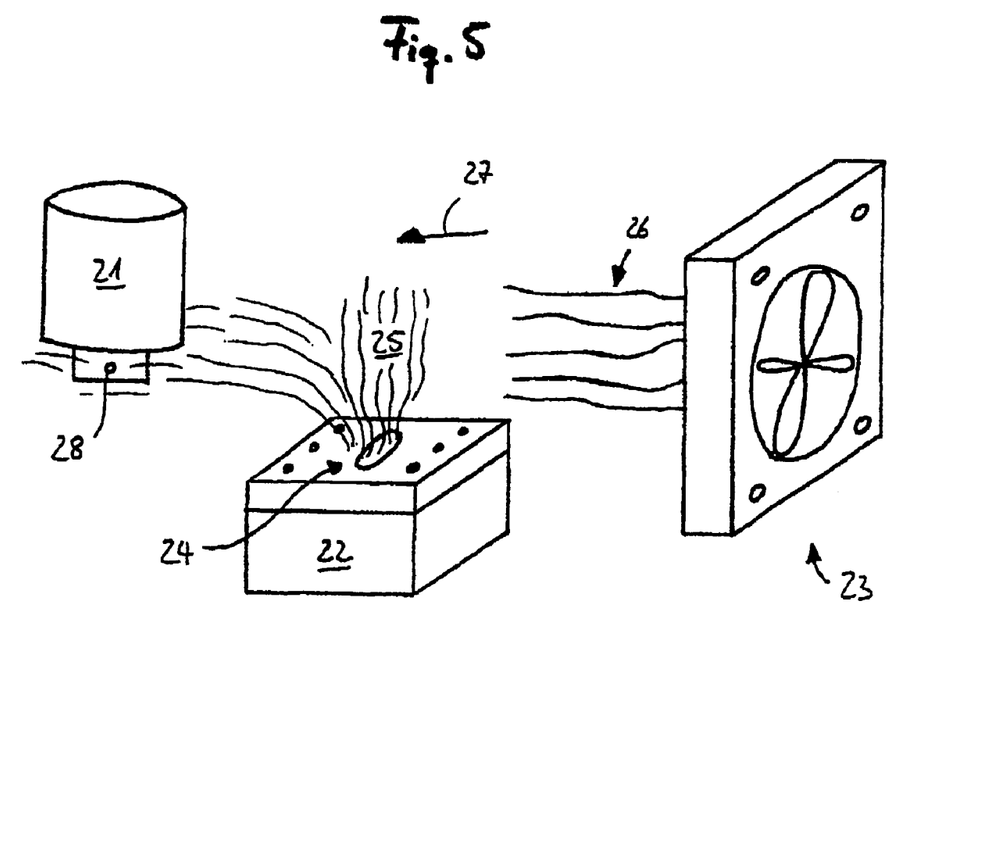
FIG. 5 a schematic representation of a mobile flue gas generator according to the invention, FIG. 6 a mobile flue gas generator in interaction with a flue gas indicator, FIG. 7 schematically, a lengthwise cross-section through a mobile flue gas generator, FIG. 8 a perspective view of a housing of a mobile flue gas generator, FIG. 9 schematically, a front view of an alternative housing of another mobile flue gas generator, FIG. 10 schematically, a side view of the alternative housing of FIG. 9, FIG. 11 schematically, a rear view of the alternative housing of FIGS. 9 and 10, FIG. 12 schematically, a top view of the alternative housing of FIGS. 9 to 11, and FIG. 13 schematically, a perspective view of the alternative housing of FIGS. 9 to 12.

In the representation according to FIG. 5, the arrangement of a flue gas indicator 21, a heat chamber 22, and a fan 23 is shown. A flue gas 25 gets into the environment through an opening 24 of the heat chamber 22. The fan 23 blows a stream of air 26 in the direction of the arrow 27. In this connection, the flue gas 25 is entrained and registered by a detector 28 of the flue gas indicator 21, thereby initiating an alarm signal. Once the test of the flue gas indicator 21 has been completed, the development of the flue gas 25 in the heat chamber 22 is stopped, in that the electric heating device is shut off. The air stream 26 of the fan 23 blows the flue gas indicator 21, particularly the detector 28 of the flue gas indicator 21, clear of remaining flue gas particles.

Figure 6:
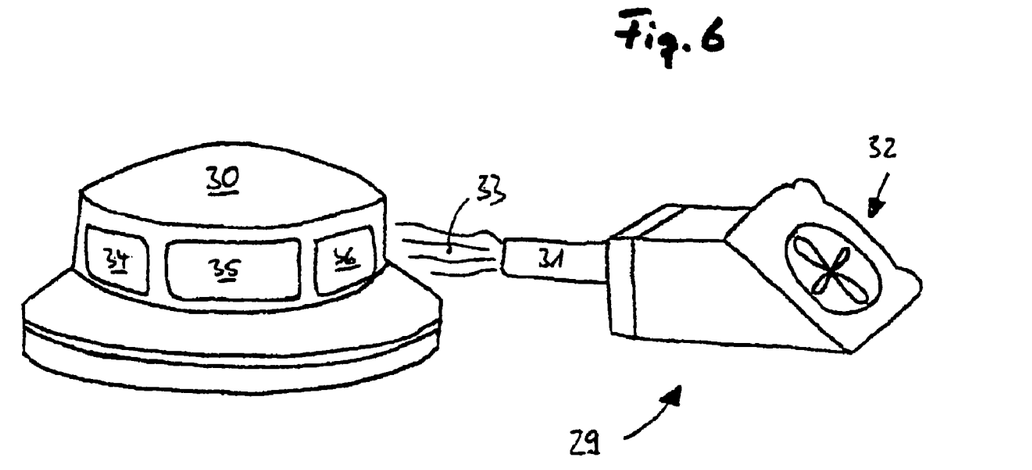

In FIG. 6, a mobile flue gas generator 29 is held in the immediate vicinity of a flue gas indicator 30. In this connection, the mobile flue gas generator 29 has a tube 31 in its front region and a fan 32 in its back region. In the interior of the mobile flue gas generator 29, there is a heat chamber 22, as described above, for generating flue gas. An air stream transported by the fan 32 blows flue gas 33 generated in the mobile flue gas generator in the direction of the flue gas indicator 30. In this connection, the flue gas indicator 30 has openings 34, 35, and 36, through which the flue gas 33 gets to a detector of the flue gas indicator. Accurate aiming to produce flow against a flue gas indicator 30 by means of a mobile flue gas generator 29 is significantly simplified by the tube 31.

The mobile flue gas generator 37 (FIG. 7) has an elastic housing 38 in which a supply device 39 for a test medium 50, a metering device 40, a blower 41, a collection device 42, an output device 43 for the test medium 50, as well as a heating device 44 are arranged.

Figure 7:
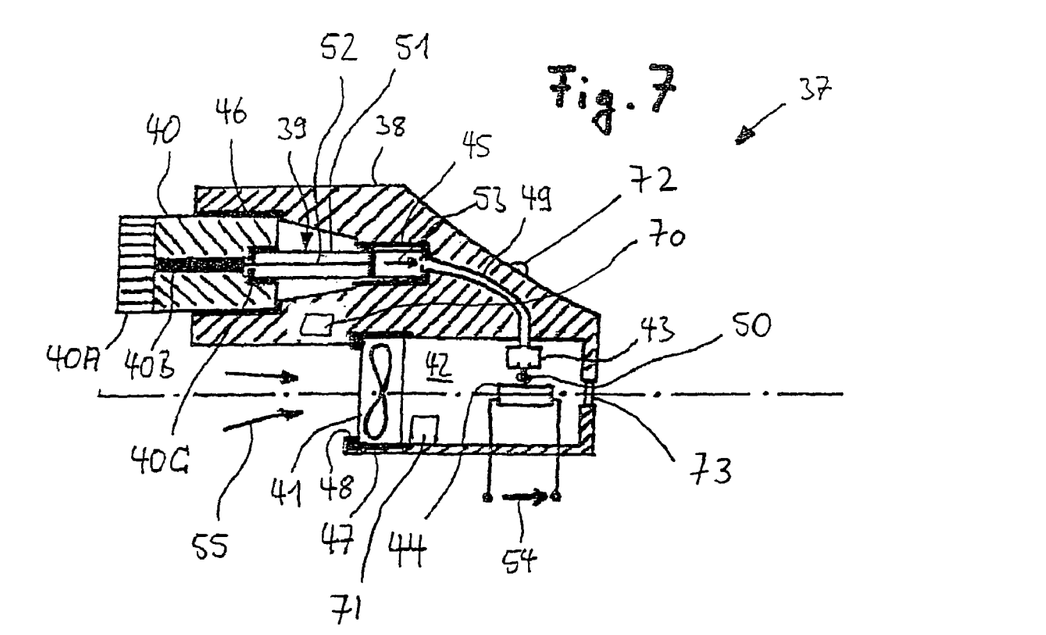

The supply device 39, the metering device 40, and the blower 41, in particular, are each arranged in a holding means 45, 46, and 47 in the housing 38, whereby the holding means 47 additionally has a rubber lip 48. The holding means 45, 46, and 47 are structured in such a manner that the supply device 39, the metering device 40, and the fan 41, respectively, can be quickly and easily plugged into them, so that these components are releasably fixed in place in or on the elastic housing 38.

The holding means 45 is connected with the output device 43 by means of a line 49, so that a test medium 50 gets from the supply device 39 to the output device 43 by means of the elastic housing 38, whereby the output device 43 issues the test medium 50 to the heating device 44. The output device 43 is arranged in the immediate vicinity of the heating device 44 for this purpose, so that for one thing, the test medium 50 exiting from the output device 43 enters directly into contact with the heating device 44, and for another thing, the heating device 44 is so far removed from the output device 43 that the output device 43 is not damaged by the heat development of the heating device 44.

In this exemplary embodiment, the supply device 39 consists of a cylinder 51, into which a piston 52 has been introduced.

By means of a setting dial 40A of the metering device 40, a mechanism 40B of the metering device 40 is set in such a manner that the mechanism 40B communicates with the piston 52 of the supply device 39 and, as needed, presses the test medium 50 in the direction of the arrow 53, out of the cylinder 51 of the supply device 39, into the line 49.

In order to securely connect the cylinder 51 of the supply device 39 with the metering device 40, the metering device 40 has a holding region 40C, into which the supply device 39 is plugged.

In order to optimally test a flue gas indicator 30 (see FIG. 6), the heating device 44 is preheated to approximately 150° C., before the test medium 50 comes into contact with the heating device 44. Particularly in order to regulate the temperature of the heating device 44, an energy flow 54 through the heating device 44 is made available discontinuously.

The test medium 50 made to smoke in the heating device 44 collects as flue gas 25 (see FIG. 5) in the collection device 42, before it is transported out of the collection device 42 by means of an air volume 55, which is drawn into the collection device by means of the activated blower 41.

The mobile flue gas generator 38 has an energy source 70 and by means of this electric energy source, a power supply to the heating device 44 and the fan 41 is guaranteed. Preferably, the electrical energy source possesses a battery or a rechargeable battery.

The collection device 42 comprises a flue gas sensor 71 to determine whether a sufficient amount of flue gas has been generated and is present in the collection device 42. Such sensors are known to the skilled person and may utilize ionization techniques or photoelectric techniques.

By activating the flue gas sensor 71, an indicator 72 gives an optical message concerning the point in time at which sufficient flue gas for testing a flue gas for testing a flue gas indicator. It will be apparent to the skilled person that such an indicator may be an LED.

A wire 73 is provided at the output of the generator 37 and has a structure which is temperature dependent. By means of such a wire 73 it is possible to activate a flap, for example, in such a manner that it closes the collection device 42 or at least partly opens it.

Figure 8:
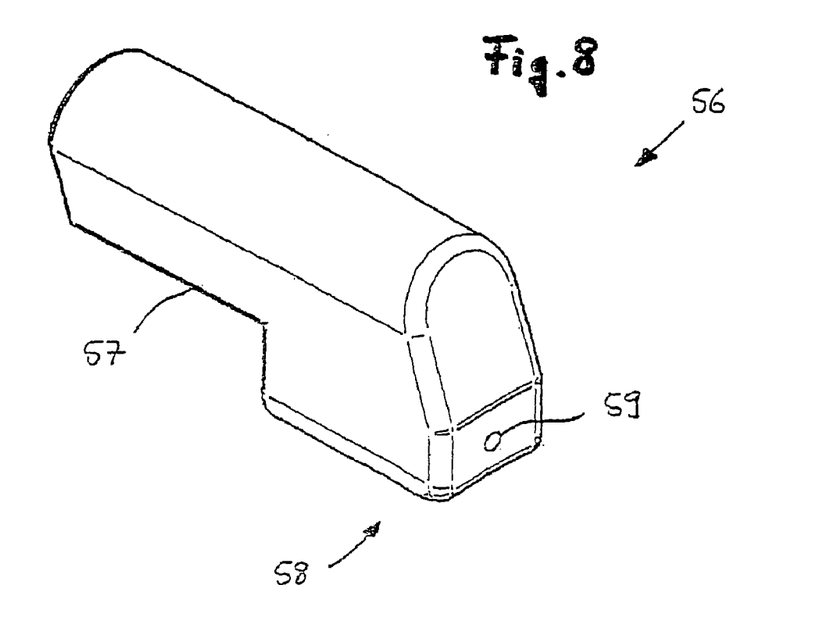
Figure 9:
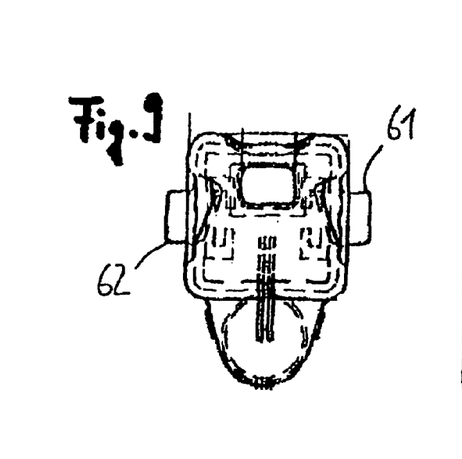
Figure 10:
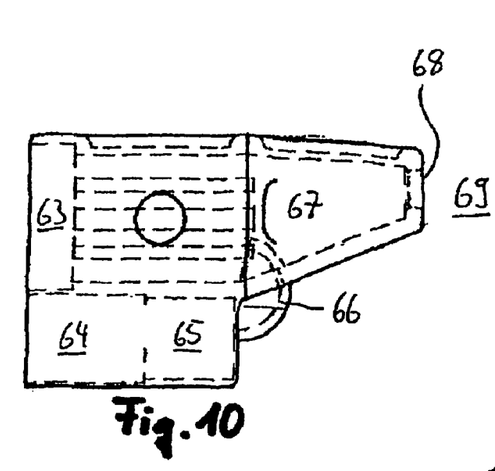
Figure 11:
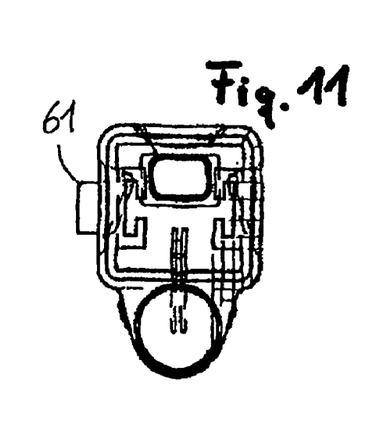
Figure 12:
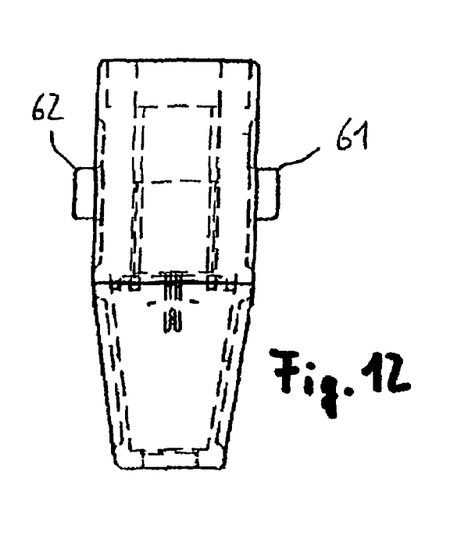
Figure 13:
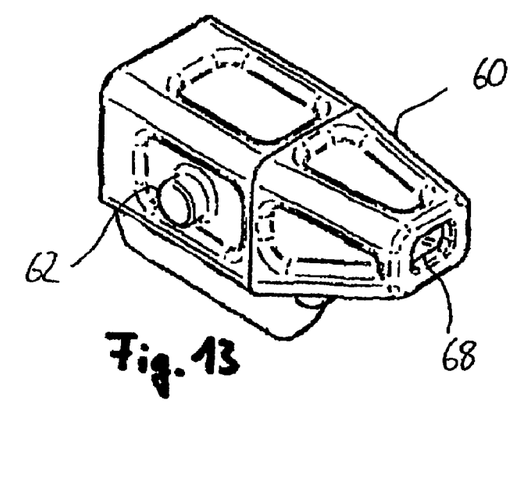

The exemplary embodiment 56 of FIG. 8 shows an elastic housing 57 of a mobile flue gas generator, whereby the elastic housing 57 has an exit opening 59 in a front region 58, from which a flue gas 25 that has been generated (see FIG. 5) exits from the elastic housing 57.

The elastic housing 60 shown in FIGS. 9 to 13 comprises two holding regions 61 and 62, by way of which the elastic housing 60 is connected with a telescope-like holding device (not shown here) and is guided to a flue gas indicator 30 (see FIG. 6), for example.

The elastic housing 60 furthermore comprises a region 63 in which a blower 41 is arranged (see FIG. 7).

A metering device 40 (see FIG. 7) as well as a supply device 39 (see FIG. 7) for making available a test medium 50 (see FIG. 7) are arranged in a region 64 and 65 of the elastic housing 60.

The test medium 50 (see FIG. 7) gets into a region 67 of the elastic housing 60, in which the test medium 50 (see FIG. 7) is made to smoke, by means of a line 66. The resulting flue gas 25 (see FIG. 5) gets into an output region 69, in which a flue gas indicator 30 (see FIG. 6) is arranged, by means of an exit opening 68.

The invention claimed is:

1. A mobile hazard detector tester comprising:
    a housing including an electrical heating means, a supply means, and blowing means, the supply means arranged to supply a test medium to the heating means, wherein the heating means is arranged to heat the test medium in order to produce a flue gas, and the blowing means is adapted to provide a circulation of air in the tester and release the generated flue gas from the tester through an opening in order to perform a test on a hazard detector, wherein the tester further comprises a battery to provide power to the electrical heating means and blowing means, an accumulation chamber for at least temporarily accumulating the generated flue gas, and means for metering the volume of flue gas emitted from the accumulation chamber and supplied to the hazard detector, and at least one of the supply means, blowing means and metering means is arranged to be plugged into the housing with a positive-lock or friction-lock connection so as to be releasably attached to the housing and the supply means and blowing means are positioned within the housing.

2. The tester of claim 1, wherein the accumulation chamber has at least one inlet opening and at least one exit opening.

3. The tester of claim 2, wherein the accumulation chamber comprises means for opening and closing at least one of the openings.

4. The tester of claim 2 wherein at least one opening contains an opening device which in turn contains a wire, the form of which is temperature dependent.

5. The tester of claim 2 wherein the accumulation chamber comprises a sensing means for sensing the amount of flue gas accumulated in the accumulation chamber, and wherein the tester further comprises an indication means for indicating that a predetermined amount of flue gas is present in the accumulation chamber in response to a signal from the sensing means.

6. The tester of claim 1, wherein the test medium contains a solid or gel like material.

7. The tester of claim 1, wherein the flue gas is smoke.

8. The tester of claim 1, wherein the blowing means is adapted to accelerate the air in a pulse-like manner.

9. The tester of claim 1, wherein the blowing means is a fan.

10. The tester of claim 9 wherein the speed of rotation of the fan is adapted to be changed in order to provide a changeable volume stream of air.

11. A method of testing a hazard detector using a mobile hazard detector tester as claimed in claim 1, the method comprising:
    supplying a test medium to the heating means;
    heating the test medium thereby producing a flue gas;
    accumulating the generated flue gas in an accumulation chamber;
    activating the blowing means to circulate air in the tester; and
    expelling the flue gas from the tester discontinuously in metered volumes of flue gas after a predetermined amount of flue gas has accumulated in the accumulation chamber.

12. The mobile hazard detector tester according to claim 1, wherein the supply means comprises a cylinder and a piston disposed in said cylinder, and wherein the tester further comprises means for metering the amount of test medium supplied to the heating means connected to the cylinder, the means for metering comprising a mechanism in communication with said piston to cause the piston to press the test medium out of the cylinder to supply a metered amount of test medium to the heating means.

* * * * *